United States Patent [19]

Rentzea et al.

[11] 4,278,800

[45] Jul. 14, 1981

[54] γ-AZOLYL COMPOUNDS, AGENTS CONTAINING THEM FOR REGULATING PLANT GROWTH, AND THE MANUFACTURE THEREOF

[75] Inventors: Costin Rentzea, Heidelberg; Hubert Sauter; Eberhard Ammermann, both of Ludwigshafen; Gerd Heilen, Speyer; Johann Jung, Limburgerhof, all of Fed. Rep. of Germany

[73] Assignee: BASF Aktiengesellschaft, Fed. Rep. of Germany

[21] Appl. No.: 80,527

[22] Filed: Oct. 1, 1979

[30] Foreign Application Priority Data

Oct. 18, 1978 [DE] Fed. Rep. of Germany ....... 2845254

[51] Int. Cl.$^3$ .................. C07D 249/08; C07D 249/04
[52] U.S. Cl. .................................... 548/262; 548/255; 548/335; 548/341; 71/92; 71/90
[58] Field of Search ............................. 71/92; 548/262

[56] References Cited

U.S. PATENT DOCUMENTS

| | | | |
|---|---|---|---|
| 3,755,349 | 8/1973 | Timmler et al. | 548/262 |
| 3,870,726 | 3/1975 | Jager et al. | 548/262 |
| 3,941,800 | 3/1976 | Draber et al. | 548/262 |
| 8,647,814 | 3/1972 | Greenfield | 548/262 |

FOREIGN PATENT DOCUMENTS 2650831 6/1978 Fed. Rep. of Germany .

*Primary Examiner*—Catherine L. Mills
*Attorney, Agent, or Firm*—Keil & Witherspoon

[57] ABSTRACT

New γ-azolyl compounds, especially ethers, esters and carbamates, processes for their manufacture, agents for influencing plant growth which contain these compounds as active ingredients, and processes for regulating plant growth with these compounds.

2 Claims, No Drawings

γ-AZOLYL COMPOUNDS, AGENTS CONTAINING THEM FOR REGULATING PLANT GROWTH, AND THE MANUFACTURE THEREOF

The present invention relates to new and valuable γ-azolyl compounds, especially ethers, esters and carbamates, processes for their manufacture, agents for influencing plant growth which contain these compounds as active ingredients, and processes for regulating plant growth with these compounds.

The use of β-triazolyl ethers, such as 1-(4'-bromophenyl)-1-allyloxy-2-(1",2",4"-triazolyl-(1")-ethane, for influencing growth in rape, wheat, oats, rye and barley has been disclosed (German Laid-Open Application DE-OS No. 2,650,831). However, their action, particularly at low concentrations, is not always sufficient.

It has also been disclosed (U.S. Pat. No. 3,156,544) that 2-chloroethyltrimethylammonium chloride (chlorocholine chloride, CCC) has growth-regulating properties. It helps for instance to reduce growth height in some cereal species and to inhibit vegetative growth in some other crop plants. However, the action of this compound, particularly at low application rates, is not always satisfactory.

We have now found that compounds of the formula

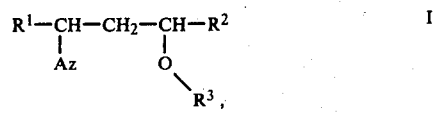
  I, where $R^1$ and $R^2$ are identical or different and each denotes alkyl of 1 to 8 carbon atoms, furanyl, thienyl, naphthyl, or phenyl, phenyl being unsubstituted or substituted by fluoro, chloro, bromo, nitro, trifluoromethyl, alkyl of 1 to 4 carbon atoms, alkoxy of 1 to 4 carbon atoms, or by alkenyl of 1 to 4 carbon atoms, $R^3$ denotes alkyl of 1 to 8 carbon atoms, unsubstituted or chloro-substituted alkenyl of 2 to 5 carbon atoms, alkynyl of 3 to 4 carbon atoms, benzyl which is unsubstituted or substituted by fluoro, chloro, bromo, nitro, trifluoromethyl, or by alkyl or alkoxy of 1 to 4 carbon atoms, $R^3$ further denotes —CO—$R^4$, $R^4$ denoting alkyl of 1 to 5 carbon atoms which is unsubstituted or substituted by halogen, alkoxy, oxo (=O) or carboxyalkyl, or $R^4$ denoting an aromatic radical, and $R^3$ further denotes —CO—NH—$R^5$, $R^5$ denoting alkyl of 1 to 4 carbon atoms or an aromatic radical, and Az denotes imidazolyl, 1,2,4-triazolyl or 1,2,3-triazolyl, exercise an excellent influence on plant growth and are very well tolerated by crop plants.

Examples of meanings for $R^1$ and $R^2$ are methyl, n-propyl, isopropyl, n-butyl, sec-butyl, isobutyl, tert-butyl, 3-pentyl, neopentyl, 2-furanyl, 2-thiophenyl, 4-fluorophenyl, 2- and 4-chlorophenyl, 2,4-dichlorophenyl, 4-bromophenyl, p-tolyl, 2- and 4-methoxyphenyl, 4-isopropylphenyl and 1-naphthyl.

Examples of meanings for $R^3$ are methyl, ethyl, n-propyl, allyl, propargyl, n-butyl, 1-crotyl, n-pentyl, 3-methyl-2-buten-1-yl, n-hexyl, n-octyl, 1-(carbomethoxy)-1-ethyl, benzyl, 4-fluorobenzyl, 4-chlorobenzyl, 2,4-dichlorobenzyl, 3- and 4-bromobenzyl, 4-methylbenzyl, 4-tert-butylphenyl and 4-methoxybenzyl.

Examples of meanings for —CO—$R^4$ are acetyl, chloroacetyl, propionyl, butyryl, acetoacetyl, pivaloyl and benzoyl.

Examples of meanings for —CO—NH—$R^5$ are methylcarbamoyl and 4-chlorophenylcarbamoyl.

Az denotes for instance 1-imidazolyl and, preferably, 1,2,4-triazol-1-yl.

We have further found that γ-azolyl compounds of the formula I are obtained by reaction of γ-azolyl alcoholates of the formula

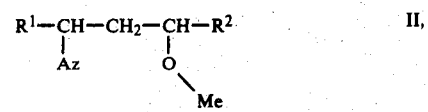
  II, where $R^1$, $R^2$ and Az have the above meanings and Me denotes sodium or potassium, with organohalides of the formula

  III, where $R^3$ has the above meanings and X denotes chlorine, bromine or iodine, preferably chlorine or bromine. This reaction is carried out for example in an indifferent diluent such as ethyl ether, tetrahydrofuran, dioxane, toluene, xylene or dimethylformamide, at from 0° to +100° C., preferably from 30° to 50° C.

The γ-azolyl alcoholates of the formula II are readily obtained from γ-azolyl alkanols of the formula

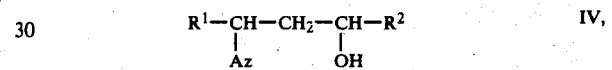
  IV, where $R^1$, $R^2$ and Az have the above meanings, with strong bases such as alkali metal hydrides, alkali metal amides or lower alkali metal alcoholates; in the latter case, the lower alcohols which are formed have to be removed by azeotropic distillation. Particularly suitable for this purpose are molar amounts, or excesses of up to 50%, of lithium hydride, sodium hydride, sodium amide, sodium methoxide, sodium ethoxide and potassium tert-butoxide. It is generally not necessary to isolate the alkali metal salts II. They may, in an inert soovent, e.g., toluene, xylene, tetrahydrofuran, dioxane, or dimethylformamide, be further reacted immediately after manufacture with the compounds of the formula III. If phase transfer catalysts, such as benzyl triethylammonium chloride, tetrabutylammonium methosulfate or tetrapentylphosphonium bromide, are used, aqueous liquors, e.g., 50% strength sodium hydroxide solution, may be employed. The compounds of the formula III are then used in a 10- to 20-fold molar excess, and also act as diluents. These reactions are carried out at from about 0° to +90° C., preferably from 10° to 50° C.

The compounds of the formula I according to the invention are also obtained by reaction of γ-azolyl alcohols of the formula IV with acid chlorides or acid anhydrides of the formula

  V, where $R^4$ has the above meanings and Y denotes chlorine, bromine or —O—CO—$R^4$, or with isocyanates of the formula

  VI or with carbamoyl chlorides of the formula

R⁵—NH—COCl    VII, where R⁵ has the above meanings, in the presence or absence of a basic catalyst or of an acid binder and in the presence or absence of a diluent.

The γ-azolyl alcohols to be used as starting materials are defined in general terms by formula IV. They are obtained for example by reduction of prior art 8-azolyl ketones (cf. German Laid-Open Applications DE-OS No. 2,634,511 and 2,656,728) of the formula

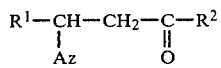    VIII, where R¹, R² and Az have the above meanings. The reduction may be effected for instance as follows:

(a) with complex hydrides, such as sodium borohydride, in the presence of a polar solvent, e.g., methanol, or with lithium alanate in diethyl ether, tetrahydrofuran or dioxane, at from 0° to 30° C.; or (b) with hydrogen in the presence of a catalyst, such as platinum or Raney nickel, and in the presence of a polar solvent, such as methanol, ethanol or isopropanol, at from 40° to 60° C. and a pressure of from 1 to 100 bars; or (c) with aluminum isopropylate in the presence of an inert solvent, e.g., isopropanol, at from 40° to 120° C., followed by hydrolysis, e.g., with aqueous hydrochloric acid.

Diastereoisomeric mixtures are formed because compounds of the formula IV have 2 chiral carbon atoms, and they may therefore be in the erythro- or threo-form. In both cases they are racemates. With some of the γ-azolyl alcohols and some of the compounds of the formula I according to the invention prepared therefrom, the erythro- and threo-forms may be separated, for example as a result of differences in solubility or by column chromatography, and isolated in pure form.

The organohalides of the formula III, the acid chlorides and acid anhydrides of the formula V, the isocyanates of the formula VI and the carbamoyl chlorides of the formula VII required for the manufacture of the active ingredients according to the invention are known or may be prepared by conventional methods described in general textbooks on organic chemistry.

The reaction of γ-azolyl alcohols of the formula IV with starting materials of the formulae V, VI and VII is advantageously carried out without a diluent, or in an inert solvent. Examples are acetonitrile; ethers, such as diethyl ether, dipropyl ether, dibutyl ether, tetrahydrofuran, dioxane and dimethoxyethane; esters, such as ethyl acetate; ketones, such as acetone and methyl ethyl ketone; chlorinated hydrocarbons, such as methylene chloride, chloroform, carbon tetrachloride, dichloroethane, tetrachloroethane and chlorobenzene; and hydrocarbons, such as benzene, toluene and xylene.

It is advantageous to add, as auxiliary base or catalyst, a base, such as sodium hydroxide, sodium carbonate, potassium carbonate, calcium carbonate or sodium acetate, or an amine, such as triethylamine, pyridine, imidazole or piperidine. The reaction temperature may be varied from −25° to +100° C., and is preferably from +10° to 80° C.

The compounds of the formula I obtained in this manner are isolated by conventional methods and, if desired, purified.

Individual examples of the novel γ-azolyl compounds are as follows:
2-methoxy-4-(1,2,4-triazolyl-(1))-5,5-dimethylhexane,
2-n-propoxy-4-(1,2,4-triazolyl-(1))-5,5-dimethylhexane,
2-allyloxy-4-(1,2,4-triazolyl-(1))-5,5-dimethylhexane,
2-n-butoxy-4-(1,2,4-triazolyl-(1))-5,5-dimethylhexane,
2-n-pentyloxy-4-(1,2,4-triazolyl-(1))-5,5-dimethylhexane,
2-n-octyloxy-4-(1,2,4-triazolyl-(1))-5,5-dimethylhexane,
2-benzyloxy-4-(1,2,4-triazolyl-(1))-5,5-dimethylhexane,
2-pivaloyloxy-4-(1,2,4-triazolyl-(1))-5,5-dimethylhexane,
2,2-dimethyl-3-(1,2,4-triazolyl-(1))-5-allyloxynonane,
2,2,4,4-tetramethyl-3-(1,2,4-triazolyl-(1))-5-allyloxyheptane,
1-methoxy-1-phenyl-3-(1,2,4-triazolyl-(1))-4,4-dimethylpentane,
1-allyloxy-1-phenyl-3-(1,2,4-triazolyl-(1))-4,4-dimethylpentane,
1-methoxy-1-phenyl-3-(1,2,4-triazolyl-(1))-5-methylhexane,
1-phenyl-1-(1,2,4-triazolyl-(1))-3-ethoxybutane,
1-phenyl-1-(1,2,4-triazolyl-(1))-3-allyloxybutane,
1-phenyl-1-(1,2,4-triazolyl-(1))-3-(1-butoxy)-butane,
1-phenyl-1-(1,2,4-triazolyl-(1))-3-(1-hexyloxy)-butane,
1-phenyl-1-(1,2,4-triazolyl-(1))-3-(1-octyloxy)-butane,
1-phenyl-1-(1,2,4-triazolyl-(1))-3-benzyloxy-butane,
1-phenyl-1-(1,2,4-triazolyl-(1))-3-(4-chlorobenzyloxy)-butane,
1-phenyl-1-(1,2,4-triazolyl-(1))-3-pivaloyloxybutane,
1-(4-chlorobenzyloxy)-1-phenyl-3-(1,2,4-triazolyl-(1))-4,4-dimethylpentane,
1-methoxy-1-(4-fluorophenyl)-3-(1,2,4-triazolyl-(1))-4,4-dimethylpentane,
1-allyloxy-1-(4-fluorophenyl)-3-(1,2,4-triazolyl-(1))-4,4-dimethylpentane,
1-benzyloxy-1-(4-fluorophenyl)-3-(1,2,4-triazolyl-(1)-4,4-dimethylpentane,
1-(4-chlorobenzyloxy)-1-(4-fluorophenyl)-3-(1,2,4-triazolyl-(1))-4,4-dimethylpentane,
1-(4-methoxybenzyloxy)-1-(4-fluorophenyl)-3-(1,2,4-triazolyl-(1))-4,4-dimethylpentane,
1-acetoxy-1-(4-fluorophenyl)-3-(1,2,4-triazolyl-(1))-4,4-dimethylpentane,
1-(2-chlorophenyl)-1-(1,2,4-triazolyl-(1))-3-allyloxybutane,
1-(2-chlorophenyl-1-(1,2,4-triazolyl-(1))-3-(1-propoxy)-butane,
1-(2-chlorophenyl)-1-(1,2,4-triazolyl-(1))-3-(1-butoxy)-butane,
1-(2-chlorophenyl)-1-(1,2,4-triazolyl-(1))-3-(1-hexyloxy)-butane,
1-(2-chlorophenyl)-1-(1,2,4-triazolyl-(1))-3-allyloxy-4,4-dimethylpentane,
1-(4-chlorophenyl)-1-(1,2,4-triazolyl-(1))-3-ethoxybutane,
1-(4-chlorophenyl)-1-(1,2,4-triazolyl-(1))-3-allyloxybutane,
1-(4-chlorophenyl)-1-(1,2,4-triazolyl-(1))-3-(1-pentyloxy)-butane,
1-(4-chlorophenyl)-1-(1,2,4-triazolyl-(1))-3-(4-chlorobenzyloxy)-butane,
1-(4-chlorophenyl)-1-(1,2,4-triazolyl-(1))-3-(2,4-dichlorobenzyloxy)-butane,
1-methoxy-1-(4-chlorophenyl)-3-(1,2,4-triazolyl-(1))-4,4-dimethylpentane,
1-allyloxy-1-(4-chlorophenyl-3-(1,2,4-triazolyl-(1))-4,4-dimethylpentane, 1-allyloxy-1-(4-chlorophenyl)-3-(1,2,4-triazolyl-(1))-5-methylhexane,
1-allyloxy-1-(4-chlorophenyl)-3-(1,2,4-triazolyl-(1))-5-ethylhexane,
1-crotyloxy-1-(4-chlorophenyl)-3-(1,2,4-triazolyl-(1))-4,4-dimethylpentane,
1-(3-methyl-2-buten-1-yloxy)-1-(4-chlorophenyl)-3-(1,2,4-triazolyl-(1))-4,4-dimethylpentane,
1-propargyloxy-1-(4-chlorophenyl)-3-(1,2,4-triazolyl-(1))-4,4-dimethylpentane,
2-(1-(4-chlorophenyl)-3-(1,2,4-triazolyl-(1))-4,4-dimethyl-pentan-1-oxy)-propionic acid methyl ester,
1-benzyloxy-1-(4-chlorophenyl)-3-(1,2,4-triazolyl-(1))-4,4-dimethylpentane,
1-(4-fluorobenzyloxy)-1-(4-chlorophenyl)-3-(1,2,4-triazolyl-(1))-4,4-dimethylpentane,
1-(4-chlorobenzyloxy)-1-(4-chlorophenyl)-3-(1,2,4-triazolyl-(1))-4,4-dimethylpentane,
1-(4-bromobenzyloxy)-1-(4-chlorophenyl)-3-(1,2,4-triazolyl-(1))-4,4-dimethylpentane,
1-(4-methylbenzyloxy)-1-(4-chlorophenyl)-3-(1,2,4-triazolyl-(1))-4,4-dimethylpentane,
1-(3-trifluoromethylbenzyloxy)-1-(4-chlorophenyl)-3-(1,2,4-triazolyl-(1))-4,4-dimethylpentane,
1-(4-tert.-butylbenzyloxy)-1-(4-chlorophenyl)-3-(1,2,4-triazolyl-(1))-4,4-dimethylpentane,
1-(2,4-dichlorobenzyloxy)-1-(4-chlorophenyl)-3-(1,2,4-triazolyl-(1))-4,4-dimethylpentane,
1-acetoxy-1-(4-chlorophenyl)-3-(1,2,4-triazolyl-(1))-4,4-dimethylpentane,
1-(4-chlorophenyl-1-(1,2,4-triazolyl-(1))-3-acetoxy-4,4-dimethylpentane,
1-propionyloxy-1-(4-chlorophenyl)-3-(1,2,4-triazolyl-(1))-4,4-dimethylpentane,
1-acetylacetoxy-1-(4-chlorophenyl)-3-(1,2,4-triazolyl-(1))-4,4-dimethylpentane,
1-(methylcarbamoyl)-1-(4-chlorophenyl)-3-(1,2,4-triazolyl-(1))-4,4-dimethylpentane,
1-(4-chlorophenylcarbamoyl)-1-(4-chlorophenyl)-3-(1,2,4-triazolyl-(1))-4,4-dimethylpentane,
1-methoxy-1-(4-bromophenyl)-3-(1,2,4-triazolyl-(1))-4,4-dimethylpentane,
1-allyloxy-1-(4-bromophenyl)-3-(1,2,4-triazolyl-(1))-4,4-dimethylpentane,
1-(methoxy-1-(4-tolyl)-3-(1,2,4-triazolyl-(1))-4,4-dimethylpentane,
1-allyloxy-1-(4-tolyl)-3-(1,2,4-triazolyl-(1))-4,4-dimethylpentane,
1-methoxy-1-(4-methoxyphenyl)-3-(1,2,4-triazolyl-(1))-4,4-dimethylpentane,
1-n-propoxy-1-(4-methoxyphenyl)-3-(1,2,4-triazolyl-(1))-4,4-dimethylpentane,
1-acetoxy-1-(4-methoxyphenyl)-3-(1,2,4-triazolyl-(1))-4,4-dimethylpentane,
1-(2-methoxyphenyl)-1-(1,2,4-triazolyl-(1))-3-ethoxybutane,
1-(2-methoxyphenyl)-1-(1,2,4-triazolyl-(1))-3-allyloxybutane,
1-(2-methoxyphenyl)-1-(1,2,4-triazolyl-(1))-3-(1-butoxy)-butane,
1-(2-methoxyphenyl)-1-(1,2,4-triazolyl-(1))-3-(1-hexyloxy)-butane,
1-(2-methoxyphenyl)-1-(1,2,4-triazolyl-(1))-3-(1-octyloxy)-butane,
1-(2-methoxyphenyl)-1-(1,2,4-triazolyl-(1))-3-benzyloxy-butane,
1-(2-methoxyphenyl)-1-(1,2,4-triazolyl-(1))-3-(4-chlorobenzyloxy)-butane,
1-(2-methoxyphenyl)-1-(1,2,4-triazolyl-(1))-3-pivaloyloxy-butane,
1-(2-methoxyphenyl)-1-(1,2,4-triazolyl-(1))-3-allyloxy-4,4-dimethylpentane,
1-(2-methoxyphenyl)-1-(1,2,4-triazolyl-(1))-3-(1-butoxy)-4,4-dimethylpentane,
1-(2-methoxyphenyl)-1-(1,2,4-triazolyl-(1))-3-acetoxy-4,4-dimethylpentane,
1-(2-methoxyphenyl)-1-(1,2,4-triazolyl-(1))-3-chloroacetoxy-4,4-dimethylpentane,
1-methoxy-1-(2,4-dichlorophenyl)-3-(1,2,4-triazolyl-(1)-4,4-dimethylpentane,
1-allyloxy-1-(2,4-dichlorophenyl)-3-(1,2,4-triazolyl-(1))-4,4-dimethylpentane,
1-propargyloxy-1-(2,4-dichlorophenyl)-3-(1,2,4-triazolyl-(1))-4,4-dimethylpentane,
1-benzyloxy-1-(2,4-dichlorophenyl)-3-(1,2,4-triazolyl-(1))-4,4-dimethylpentane,
1-(2,4-dichlorophenyl)-1-(1,2,4-triazolyl-(1))-3-allyloxy-4,4-dimethylpentane,
1-(2,4-dichlorophenyl)-1-imidazolyl-3-acetoxy-4,4-dimethylpentane,
1-(4-isopropylphenyl)-1-(1,2,4-triazolyl-(1))-3-(methylcarbamoyl)-4,4-dimethylpentane,
1-methoxy-1-(1-naphthyl)-3-(1,2,4-triazolyl-(1))-4,4-dimethylpentane,
1-allyloxy-1-(1-naphthyl)-3-(1,2,4-triazolyl-(1))-4,4-dimethylpentane,
1-(1-naphthyl)-1-(1,2,4-triazolyl-(1))-3-methoxybutane,
1-(1-naphthyl)-1-(1,2,4-triazolyl-(1))-3-(1-butoxy)-butane,
1-(1-naphthyl)-1-(1,2,4-triazolyl-(1))-3-benzyloxybutane,
1-(1-naphthyl)-1-(1,2,4-triazolyl-(1))-3-allyloxy-4,4-dimethylpentane,
1-methoxy-1-(2-furanyl)-3-(1,2,4-triazolyl-(1))-4,4-dimethylpentane,
1-methoxy-1-(2-thiophenyl)-3-(1,2,4-triazolyl-(1))-4,4-dimethylpentane,
1-allyloxy-1-(2-thiophenyl)-3-(1,2,4-triazolyl-(1))-4,4-dimethylpentane,
1-(4-chlorobenzyloxy)-1-(2-thiophenyl)-3-(1,2,4-triazolyl-(1))-4,4-dimethylpentane,
1-methoxy-1,3-diphenyl-3-(1,2,4-triazolyl-(1))-propane,
1-allyloxy-1,3-diphenyl-3-(1,2,4-triazolyl-(1))-propane,
1-benzyloxy-1,3-diphenyl-3-(1,2,4-triazolyl-(1))-propane,
1-(4-chlorobenzyloxy)-1,3-diphenyl-3-(1,2,4-triazolyl-(1))-propane.

The new compounds may influence practically all development stages of a plant in different ways. They are therefore used as plant growth regulators.

The diversity of action of growth regulators depends especially on (a) the type and variety of plant;

(b) the time applied, with reference to the development stage of the plants and the time of year;

(c) the place and method of application (seed treatment, soil treatment, or application to leaves);

(d) climatic factors (temperature, precipitate);

(e) soil conditions (including fertilization);

(f) the formulation or application form of the active ingredient; and (g) the concentration at which the active ingredient is applied.

A description of some of the various possibilities of using growth regulators in agriculture and horticulture is given below.

A. With the compounds according to the invention, vegetative plant growth can be inhibited to a considerable extent, a fact which is manifested particularly in a reduction in plant height. The treated plants thus have a compact habit; furthermore, the leaf color is darker.

Of advantage in practice is for example the reduction in grass growth on roadsides, canal embankments and on areas such as parks, sportsgrounds, fruit orchards, lawns and airfields, thus reducing expensive and time-consuming mowing.

A further feature of economic interest is the increase in the rigor of crops which tend to lodge, such as cereals, Indian corn and soybeans. The shortening and strengthening of the stem thus caused reduces or eliminates the danger of lodging under unfavorable weather conditions.

The use of growth regulators is also important for inhibiting plant height and changing the time of ripening in cotton.

It is thus possible for this important crop to be harvested completely mechanically.

Growth regulators may also increase or inhibit lateral branching. This is of interest when for instance it is desired to inhibit, in tobacco plants, the formation of lateral shoots (suckers) in favor of leaf development.

With growth regulators, it is possible for instance in winter rape to considerably increase the resistance to freeze injury. On the one hand, upward growth and the development of a too luxuriant (and thus particularly frost-susceptible) leaf or plant mass are inhibited; on the other, the young rape plants are kept, in spite of favorable growth conditions, in the vegetative development stage before winter frosts begin. The danger of freeze injury is thus eliminated in plants which tend to lose prematurely their inhibition to bloom and pass into the generative phase. In other crops, too, e.g., winter cereals, it is advantageous if the plants are well tillered in the fall as a result of treatment with the compounds according to the invention, but enter winter with not too lush a growth. This is a preventive measure against increased susceptibility to freeze injury and—because of the relatively low leaf or plant mass—attack by various diseases (e.g. fungus diseases). The inhibition of vegetative growth also makes closer planting possible in numerous crops, which means an increase in yield based on the area cropped.

B. Better yields both of plants parts and plant materials may be obtained with the active ingredients according to the invention. It is thus for instance possible to induce increased formation of buds, blossom, leaves, fruit, seed grains, roots and tubers, to increase the sugar content of sugar beets, sugarcane and citrus fruit, to raise the protein content of cereals and soybeans, and to stimulate the increased formation of latex in rubber trees.

The compounds according to the invention may raise the yield by influencing plant metabolism or by promoting or inhibiting vegetative and/or generative growth.

C. Finally, it is also possible with growth regulators to shorten or lengthen growth stages and to accelerate or retard the ripening process in plant parts either before or after harvesting.

A factor of economical interest is for example the facilitation of harvesting made possible by a chemical, temporally concentrated loosening (abscission) of the adherence of stalks to the branches of citrus fruit, olive trees, and other kinds of pomes, drupes and indehiscent fruit. The same mechanism, i.e., promotion of the formation of separation layers between fruit or leaf and stem of the plant, is also responsible for a chemically induced, readily controllable defoliation of plants.

The action of the compounds according to the invention is superior to that of prior art growth regulators. This action is manifested not only in monocotyledon crops, e.g., cereals such as wheat, barley, rye, oats and rice or Indian corn, but also in dicotyledons (e.g., sunflowers, tomatoes, soybeans, grapes, cotton and, particularly, rape) and various ornamentals such as chrysanthemums, poinsettias and hibiscus.

The compounds according to the invention may be applied to the crop either by treating the seed, treating the soil, i.e., through the roots, or by spraying the leaves. Because the active ingredients are well tolerated by the crop plants, application rates may vary within a wide range.

When the active ingredients are used to treat seed, active ingredient amounts of from 0.001 to 50 g, preferably from 0.01 to 10 g, per kg of seed are generally required.

When the active ingredients are applied to the soil or foliage, amounts of from 0.1 to 12 kg/hg, preferably from 0.25 to 3 kg/ha, are generally considered to be sufficient.

The compounds of the invention can be applied in conventional formulations, e.g. solutions, emulsions, suspensions, dusts, powders, pastes and granules. The form of application depends entirely on the purpose for which the agents are being used; it should, however, ensure a fine and uniform distribution of the active ingredient. The formulations are prepared in the conventional manner, for example by diluting the active ingredient with solvents and/or carriers, with or without the addition of emulsifiers and dispersants and, where water is used as the diluent, with or without an organic auxiliary solvent. Suitable auxiliaries are, essentially, solvents, for example aromatics, e.g., xylene and benzene, chloroaromatics, e.g. chlorobenzene, paraffins, e.g. petroleum fractions, alcohols, e.g. methanol and butanol, amines, e.g. ethanolamine and dimethylformamide, and water; carriers, for example natural rock powders, e.g. kaolin, alumina, talc and chalk, and synthetic rock powders, e.g. highly disperse silica and silicates; emulsifiers, for example non-ionic and anionic emulsifiers, e.g. polyoxyethylene fatty alcohol ethers, alkylsulfonates and arylsulfonates, and dispersants, for example lignin, sulfite waste liquors and methylcellulose.

The formulations in general contain from 0.1 to 95 percent by weight of active ingredient, preferably from 0.5 to 90 percent.

The formulations, and the ready-to-use preparations obtained therefrom, e.g. solutions, emulsions, suspensions, powders, dusts, pastes or granules, are applied in the conventional manner, e.g. preemergence, postemergence, or as seed disinfectants.

The agents according to the invention may, in these application forms, also be mixed and applied with other active ingredients, e.g., herbicides, insecticides, other growth regulators, bactericides, fungicides and fertilizers. When mixed with other growth regulators, the spectrum of action is in many cases increased; with a number of these compositions, synergistic effects also occur; i.e., the action of the combination product is greater than the effect of the individual components added together.

The following examples illustrate the preparation of the new compounds.

EXAMPLE 1

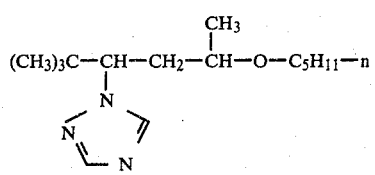

1(a) While stirring vigorously, a mixture of 9.2 g of 5,5-dimethyl-4-(1,2,4-triazolyl-(1))-hexan-2-ol, 50 g of 1-chloropentane, 2 g of tetrabutylammonium bisulfate and 32 g of 50% strength aqueous sodium hydroxide solution is heated for 20 hours at 50° C. 200 ml of water is then added to the mixture, and extraction is carried out twice, each time with 100 ml of methylene chloride. The combined extracts are shaken 8 times, each time with 100 ml of water, dried over magnesium sulfate, and concentrated in vacuo, finally at 50° C. and 0.1 mm.

There is obtained 10.5 g (79% of theory) of 2-(1-pentyloxy)-4-(1,2,4-triazolyl-(1))-5,5-dimethylhexane as a pale yellow, oily, diastereoisomeric mixture.

$^1$H NMR (80 MHz/CDCl$_3$): δ=0.7–1.5 (m, 19H, with s at 0.9, 9H), 1.5–4.6 (several m, 7H), 3.9–4.4 (2dd, tog. 1H), 7.8–8.1 ppm (4s, tog. 2 H).

Preparation of the starting compound

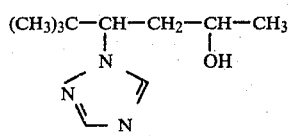

1(b) A solution of 55 g of 5,5-dimethyl-3-hexen-2-one (K. N. Campbell, J. Amer. Chem. Soc., 1980, 1937), 60 g of 1,2,4-triazole and 5 g of potassium hydroxide in 300 ml of ethanol is refluxed for 2 hours. After the solvent has been distilled off in vacuo, the residue is taken up in 300 ml of methylene chloride, washed 3 times, each time with 100 ml of water, dried over magnesium sulfate and concentrated. The residue is stirred at 0° C. with 100 ml of diisopropyl ether, and the white crystalline precipitate is filtered and dried.

There is obtained 83 g (97% of theory) of 5,5-dimethyl-4-(1,2,4-triazolyl-(1))-hexan-2-one; m.p.: 75°–76° C.

1(c) At 20° C. and while stirring well, 13.5 g of sodium borohydride is added in portions to a solution of 54 g of 5,5-dimethyl-4-(1,2,4-triazolyl-(1))-hexan-2-one in 500 ml of ethanol. After the mixture has been stirred for 17 hours at 20° C., it is concentrated. The residue is stirred for 1 hour with 270 ml of 20% strength potassium hydroxide solution and extracted with 500 ml of ether. The ether phase is dried over magnesium sulfate and concentrated. The colorless oil which remains crystallizes completely after standing for 3 days. 44.8 g (83% of theory) of 5,5-dimethyl-4-(1,2,4-triazolyl-(1))-hexan-2-ol is isolated as white crystals; m.p.: 73°–75° C.

EXAMPLE 2

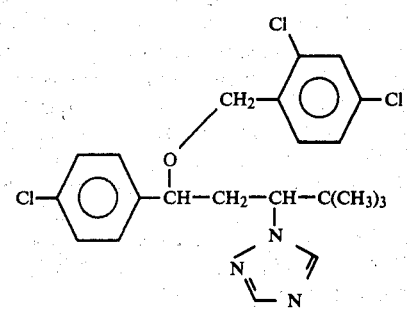

2(a) A solution of 20.5 g of 1-(4-chlorophenyl)-3-(1,2,4-triazolyl-(1))-4,4-dimethylpentan-1-ol in 100 ml of tetrahydrofuran is dripped into a suspension of 2.4 g of sodium hydride in 100 ml of anhydrous tetrahydrofuran. After the mixture has been stirred for 24 hours at room temperature, a solution of 15.7 g of 2,4-dichlorobenzyl chloride in 50 ml of tetrahydrofuran is added dropwise.

After the mixture has been stirred for 48 hours, it is carefully decomposed with 30 ml of water and the whole concentrated. The residue is taken up in 300 ml of ether, and washed 3 times, each time with 100 ml of water, and the ether phase is dried and concentrated. 25 ml of petroleum ether and 25 ml of ether are added to the residue and the mixture is left overnight at 0° C. The colorless crystalline precipitate is filtered, washed with petroleum ether and dried.

There is obtained 24.9 g (79% of theory) of 1-(2,4-dichlorobenzyloxy)-1-(4-chlorophenyl)-3-(1,2,4-triazolyl-(1))-4,4-dimethylpentane; m.p.: 104°–107° C.

Preparation of the starting compound

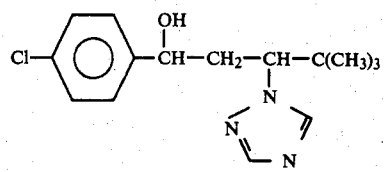

2(b) As in Example 1(c), 1-(4-chlorophenyl)-3-(1,2,4-triazolyl-(1))-4,4-dimethylpentan-1-ol was obtained as a glass-clear resin in 81% yield from the corresponding β-triazolyl ketone by reduction with sodium borohydride.

1-(4-chlorophenyl)-3-(1,2,4-triazolyl-(1))-2,2-dimethylpentan-1-one is obtained by reaction of 1-(4-chlorophenyl)-4,4-dimethyl-2-pentan-1-one with 1,2,4-triazole; yield: 86%; m.p.: 120°–122° C.

EXAMPLE 3

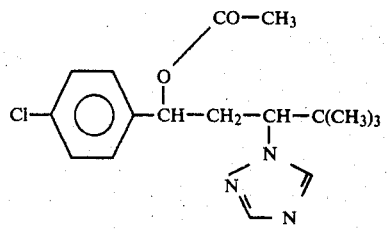

A mixture of 20.5 g of 1-(4-chlorophenyl)-3-(1,2,4-triazolyl-(1))-4,4-dimethylpentan-1-ol, 1 g of imidazole and 50 g of acetic anhydride is stirred for 3½ hours at 100° C., and then stirred into 250 ml of ice water. The aqueous suspension is extracted 3 times, each time with 100 ml of ether. The combined ether extracts are stirred for 15 minutes with 200 ml of a 6% strength sodium bicarbonate solution, and the organic phase is separated, dried over sodium sulfate and concentrated. The colorless solid residue is stirred with petroleum ether and filtered.

There is obtained 18.7 g (85% of theory) of 1-acetoxy-1-(4-chlorophenyl)-3-(1,2,4-triazolyl-(1))-4,4-dimethylpentane; m.p.: 138°–140° C.

EXAMPLE 4

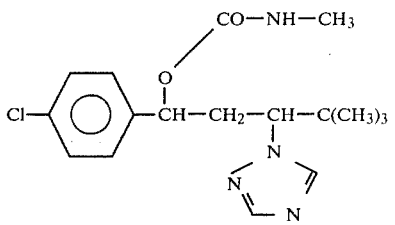

At room temperature, 0.5 ml of triethylamine and subsequently 6 g of methyl isocyanate are dripped into a solution of 17 g of 1-(4-chlorophenyl)-3-(1,2,4-triazolyl-(1))-4,4-dimethylpentan-1-ol in 50 ml of anhydrous tetrahydrofuran.

After the mixture has been stirred for 3 hours, it is (4 hours at 50° C. and 0.01 mm) concentrated in vacuo.

There is obtained 20 g (98% of theory) of 1-(methylcarbamoyl)-1-(4-chlorophenyl)-3-(1,2,4-triazolyl-(1))-4,4-dimethylpentane as a pale yellow resin.

The compounds listed in Table 1 below may be prepared analogously.

TABLE $$R^1-CH-CH_2-CH-R^2$$
$$\;\;\;\;\;\;\;\;|\;\;\;\;\;\;\;\;\;\;\;\;\;\;\;\;|$$
$$\;\;\;\;\;\;\;\;Az\;\;\;\;\;\;\;\;\;\;\;O-R^3$$

| Ex. no. | $R^1$ | $R^2$ | $R^3$ | Az | m.p./°C. | IR (film) [cm$^{-1}$] |
|---|---|---|---|---|---|---|
| 5 | $(CH_3)_3C-$ | $CH_3-$ | $CH_3-$ | 1,2,4-triazol-1-yl | oil | 2960, 1499, 1364, 1269, 1137, 1088, 732 |
| 6 | $(CH_3)_3C-$ | $CH_3-$ | $n-C_3H_7$ | " | oil | 2980, 1505, 1374, 1277, 1147, 1105, 1014, 689 |
| 7 | $(CH_3)_3C-$ | $CH_3-$ | allyl | " | oil | 2950, 1493, 1362, 1264, 1132, 1058, 1001, 911, 675 |
| 8 | $(CH_3)_3C-$ | $CH_3$ | $n-C_4H_9$ | " | oil | 2985, 2895, 1511, 1380, 1282, 1153, 1112, 1022, 693, 675 |
| 9 | $(CH_3)_3C-$ | $CH_3-$ | $n-C_8H_{17}$ | " | oil | 2950, 2920, 2845, 1496, 1366, 1268, 1135, 1095, 1067, 678 |
| 10 | $(CH_3)_3C-$ | $CH_3-$ | $C_6H_5-CH_2-$ | " | oil | 2955, 1493, 1449, 1366, 1135, 1090, 732, 695, 678 |
| 11 | $C_6H_5-$ | $CH_3-$ | $C_2H_5-$ | " | oil | 2960, 1497, 1370, 1270, 1137, 1093, 1075, 1005, 699, 678, 662 |
| 12 | $C_6H_5-$ | $CH_3-$ | allyl | " | oil | 2960, 1596, 1268, 1134, 1065, 1003, 920, 727, 696, 677, 660 |
| 13 | $C_6H_5-$ | $CH_3-$ | $n-C_4H_9$ | " | oil | 2955, 2925, 2865, 1497, 1270, 1136, 1085, 1006, 698, 678, 663 |
| 14 | $C_6H_5-$ | $CH_3-$ | $n-C_8H_{17}$ | " | oil | 2915, 2845, 1495, 1451, 1373, 1270, 1136, 1094, 1004, 698, 678, 661 |
| 15 | $C_6H_5-$ | $CH_3-$ | $C_6H_5-CH_2-$ | " | oil | 2960, 1493, 1449, 1269, 1135, 1092, 1065, 732, 696, 678 |
| 16 | $C_6H_5-$ | $CH_3-$ | $Cl-C_6H_4-CH_2-$ | " | oil | 2955, 1485, 1267, 1133, 1083, 1010, 803, 696 |
| 17 | $(CH_3)_3C-$ | $C_6H_5$ | $CH_3-$ | " | resin | 3105, 3020, 2960, 2867, 1500, 1365, 1270, 1198, 1198, 1100, 760, 705, 680 |
| 18 | $(CH_3)_3C-$ | $C_6H_5-$ | allyl | " | resin | 3080, 3020, 2950, 2865, 1500, 1368, 1270, 1138, 1005, 764, 703, 681 |
| 19 | $(CH_3)_3C-$ | $C_6H_5-$ | $Cl-C_6H_4-CH_2-$ | " | resin | 3018, 2975, 2860, 1495, 1486, 1270, 1195, 1135, 1084, 1010, 805, 760, 700, 680 |
| 20 | $(CH_3)_2CH-CH_2$ | $C_6H_5-$ | $CH_3-$ | " | oil | 3020, 2950, 2920, 2860, 1498, 1450, 1270, 1197, 1138, 1100, 1003, 758, |

TABLE-continued $$R^1-\underset{Az}{CH}-CH_2-\underset{O-R^3}{CH}-R^2$$

| Ex. no. | R¹ | R² | R³ | Az | m.p./°C. | IR (film) [cm⁻¹] |
|---|---|---|---|---|---|---|
| | | | | | | 700, 668 |
| 21 | $C_6H_5-$ | $C_6H_5-$ | $CH_3-$ | " | resin | 3105, 3083, 3060, 3030, 2928, 2820, 1500, 1453, 1273, 1200, 1137, 1100, 760, 700, 576 |
| 22 | $C_6H_5-$ | $C_6H_5-$ | $CH_2=CH-CH_2-$ | " | resin | 3055, 3022, 2920, 2855, 1495, 1450, 1280, 1125, 1004, 698 |
| 23 | $C_6H_5$ | $C_6H_5$ | $C_6H_5-CH_2-$ | " | resin | 3080, 3055, 3023, 2960, 2922, 2884, 1596, 1500, 1450, 1282, 1196, 1085, 1005, 750, 700, 565 |
| 24 | $C_6H_5$ | $C_6H_5$ | $Cl-C_6H_4-CH_2-$ | " | resin | 3057, 3022, 2920, 2862, 1595, 1478, 1270, 1195, 1135, 1086, 1010, 805, 755, 700, 570 |
| 25 | $(CH_3)_3C-$ | $F-$ | $CH_3-$ | " | resin | 2955, 1597, 1496, 1267, 1214, 1132, 1090, 832, 676 |
| 26 | $(CH_3)_3C-$ | $F-$ | $CH_2=CH-CH_2-$ | " | resin | 2952, 1597, 1495, 1265, 1130, 1073, 1002, 830, 674 |
| 27 | $(CH_3)_3C-$ | $F-$ | $C_6H_5-CH_2-$ | " | resin | 2953, 1593, 1490, 1264, 1211, 1130, 1063, 1000, 829, 728, 690, 673 |
| 28 | $(CH_3)_3C-$ | $F-$ | $Cl-C_6H_4-CH_2-$ | " | resin | 2957, 1596, 1493, 1277, 1217, 1132, 1077, 1006, 832, 802, 675 |
| 29 | $(CH_3)_3C-$ | $F-$ | $CH_3O-C_6H_4-CH_2-$ | " | resin | 2951, 1599, 1495, 1234, 1072, 1027, 830, 675 |
| 30 | 2-Cl-$C_6H_4-$ | $CH_3-$ | | " | resin | 2965, 1500, 1442, 1272, 1137, 1056, 1036, 1004, 753, 679, 658 |
| 31 | 2-Cl-$C_6H_4-$ | $CH_3-$ | $n-C_3H_7$ | " | resin | 2955, 2920, 2855, 1496, 1268, 1133, 1032, 750, 675, 654 |
| 32 | 2-Cl-$C_6H_4-$ | $CH_3$ | $n-C_4H_9$ | " | resin | 2945, 2920, 2855, 1593, 1266, 1130, 1085, 1031, 746, 674, 652 |
| 33 | 2-Cl-$C_6H_4-$ | $CH_3-$ | $n-C_6H_{13}$ | " | resin | 2950, 2920, 2850, 1496, 1269, 1132, 1089, 784, 676 |
| 34 | 4-Cl-$C_6H_4-$ | $CH_3-$ | $C_2H_5-$ | " | resin | 2965, 1489, 1370, 1271, 1136, 1008, 1011, 845, 677 |
| 35 | 4-Cl-$C_6H_4-$ | $CH_3-$ | $CH_2=CH-CH_2-$ | " | resin | 2960, 1488, 1371, 1269, 1133, 1086, 1011, 923, 676 |
| 36 | 4-Cl-$C_6H_4-$ | $CH_3-$ | $n-C_5H_{11}$ | " | resin | 2950, 2920, 2860, 1588, 1370, 1269, 1135, 1086, 1011, 676 |
| 37 | 4-Cl-$C_6H_4-$ | $CH_3-$ | $Cl-C_6H_4-CH_2-$ | " | resin | 2960, 1592, 1484, 1268, 1131, 1083, 1009, 803, 675 |
| 38 | 4-Cl-$C_6H_4-$ | $CH_3-$ | 2,4-Cl$_2$-$C_6H_3-CH_2-$ | " | resin | 1587, 1488, 1469, 1374, 1270, 1135, 1087, 1044, 1011, 813, 676 |
| 39 | 4-Cl-$C_6H_4-$ | $(CH_3)_3C-$ | $CH_3-CO-$ | " | 110–112 | |
| 40 | $(CH_3)_3C-$ | 4-Cl-$C_6H_4-$ | $CH_3-$ | " | 120–122 | |

TABLE-continued $$R^1-CH-CH_2-CH-R^2$$
$$\phantom{R^1-CH}|\phantom{-CH_2-}|$$
$$\phantom{R^1-CH}Az\phantom{-CH_2-}O-R^3$$

| Ex. no. | R¹ | R² | R³ | Az | m.p./°C. | IR (film) [cm⁻¹] |
|---|---|---|---|---|---|---|
| 41 | (CH₃)₃C— | Cl—C₆H₄— | —CH₂—CH=CH₂ | " | resin | 3100, 2978, 2860, 1590, 1495, 1484, 1425, 1366, 1268, 1196, 1136, 1085, 1010, 830, 668 |
| 42 | (CH₃)₂CH—CH₂— | Cl—C₆H₄— | —CH₂—CH=CH₂ | " | resin | 3100, 2956, 2865, 1592, 1500, 1486, 1272, 1197, 1138, 1087, 1012, 830, 670, 570 |
| 43 | (C₂H₅)₂CH— | Cl—C₆H₄— | —CH₂—CH=CH₂ | " | resin | 2955, 2926, 2870, 1590, 1496, 1433, 1270, 1194, 1136, 1086, 828, 670 |
| 44 | (CH₃)₃C— | Cl—C₆H₄— | —CH₂—CH=CH—CH₃ | " | 99–101 | |
| 45 | (CH₃)₃C— | Cl—C₆H₄— | —CH₂—CH=C(CH₃)₂ | " | resin | 2960, 2870, 1592, 1497, 1485, 1368, 1272, 1138, 1085, 1012, 830, 680, 670 |
| 46 | (CH₃)₃C— | Cl—C₆H₄— | HC≡C—CH₂— | " | resin | 3118, 2960, 2870, 2115, 1595, 1500, 1488, 1368, 1272, 1200, 1138, 1080, 1015, 830, 660 |
| 47 | (CH₃)₃C— | Cl—C₆H₄— | CH₃<br>\|<br>—CH—COOCH₃ | " | resin | 2972, 2865, 1738, 1600, 1498, 1485, 1365, 1268, 1200, 1135, 1010, 828, 680, 665 |
| 48 | (CH₃)₃C— | Cl—C₆H₄— | C₆H₅—CH₂— | " | resin | 3058, 2960, 2868, 1593, 1500, 1486, 1368, 1272, 1198, 1138, 1090, 1070, 1015, 832, 735, 700 |
| 49 | (CH₃)₃C— | Cl—C₆H₄— | F—C₆H₄—CH₂— | " | resin | 2975, 2865, 1598, 1505, 1280, 1220, 1137, 1085, 1010, 825, 680, 670, 500 |
| 50 | (CH₃)₃C— | Cl—C₆H₄— | Cl—C₆H₄—CH₂— | " | 73–76 | |
| 51 | (CH₃)₃C— | Cl—C₆H₄— | Br—C₆H₄—CH₂— | " | 90–92 | |
| 52 | (CH₃)₃C— | CH₃O—C₆H₄— | n-C₃H₇— | " | resin | 2950, 2861, 1605, 1504, 1240, 1166, 1133, 1082, 1029, 828, 675 |
| 53 | (CH₃)₃C— | Cl—C₆H₄— | H₃C—C₆H₄—CH₂— | " | 56–59 | |
| 54 | (CH₃)₃C— | Cl—C₆H₄— | 3-Br—C₆H₄—CH₂— | " | resin | 2975, 2860, 1590, 1495, 1325, 1268, 1192, 1160, 1120, 1084, 1070, 828, 792, 698 |
| 55 | (CH₃)₃C— | Cl—C₆H₄— | (CH₃)₃C—C₆H₄—CH₂— | " | resin | 2950, 2855, 1590, 1495, 1482, 1470, 1362, 1265, 1192, 1132, 1080, 830, 677, 665, 572 |
| 56 | (CH₃)₃C— | CH₃O—C₆H₄— | CH₃—CO— | " | resin | 2952, 1730, 1606, 1509, 1366, 1235, 1171, 1027, 829, 678 |
| 57 | (CH₃)₃C— | Cl—C₆H₄— | CH₃—CH₂—CO— | " | 78–80 | |
| 58 | (CH₃)₃C— | Cl—C₆H₄— | CH₃—CO—CH₂—CO— | " | resin | 3110, 2974, 1736, 1710, 1496, 1487, 1360, 1310, 1135, 1085, 1009, 825, 678 |
| 59 | (CH₃)₃C— | F—C₆H₄— | CH₃—CO— | " | 88–91 | |
| 60 | (CH₃)₃C— | Cl—C₆H₄— | Cl—C₆H₄—NH—CO— | " | resin | 3115, 2960, 1725, 1596, 1490, 1305, 1220, 1090, 1011, 826, 680, 666, 508 |
| 61 | (CH₃)₃C— | Br—C₆H₄— | CH₃— | " | 118–120 | |
| 62 | (CH₃)₃C— | Br—C₆H₄— | —CH₂—CH=CH₂ | " | oil | 3100, 2960, 2870, 1588, 1500, 1482, 1366, 1270, 1136, 1075, 1010, 825, 680, 665, 570 |

TABLE-continued $$R^1-\underset{\underset{Az}{|}}{CH}-CH_2-\underset{\underset{O-R^3}{|}}{CH}-R^2$$

| Ex. no. | R¹ | R² | R³ | Az | m.p./°C. | IR (film) [cm⁻¹] |
|---|---|---|---|---|---|---|
| 63 | $(CH_3)_3C-$ | $H_3C-\phenyl-$ | $CH_3-$ | " | 90–91 | |
| 64 | $(CH_3)_3C-$ | $H_3C-\phenyl-$ | allyl | " | resin | 2950, 2860, 1510, 1500, 1270, 1198, 1137, 1080, 1006, 923, 820, 682, 665, 582 |
| 65 | $(CH_3)_3C-$ | 3,4-Cl₂-phenyl | $CH_3-$ | " | 84–86 | |
| 66 | $(CH_3)_3C-$ | 3,4-Cl₂-phenyl | allyl | " | oil | 2960, 2865, 1586, 1500, 1466, 1368, 1270, 1138, 1090, 1042, 824, 680, 590 |
| 67 | $(CH_3)_3C-$ | 3,4-Cl₂-phenyl | $HC=CH_2-$ | " | 148–150 | |
| 68 | $(CH_3)_3C-$ | 3,4-Cl₂-phenyl | $C_6H_5-CH_2-$ | " | resin | 3025, 2955, 2865, 1584, 1498, 1466, 1368, 1270, 1136, 1085, 823, 740, 699 |
| 69 | 3,4-Cl₂-phenyl | $(CH_3)_3C-$ | $CH_3-CO-$ | imidazol-1-yl | resin | 3100, 2966, 1728, 1582, 1460, 1365, 1230, 1103, 1040, 1018, 815, 658 |
| 70 | 3,4-Cl₂-phenyl | $(CH_3)_3C-$ | allyl | 1,2,4-triazol-1-yl | resin | 3080, 2950, 2860, 1586, 1558, 1498, 1470, 1271, 1192, 1135, 923, 822, 680 |
| 71 | 4-$(CH_3)_2CH-$phenyl | $(CH_3)_3C-$ | $CH_3-NH-CO-$ | " | resin | 2955, 2870, 1705, 1500, 1418, 1362, 1260, 1135, 1000, 956, 770, 678, 658 |
| 72 | 2-OCH₃-phenyl | $(CH_3)_3C-$ | allyl | " | resin | 2950, 1490, 1243, 1135, 1072, 752, 662 |
| 73 | 2-OCH₃-phenyl | $(CH_3)_3C-$ | $n-C_4H_9$ | " | resin | 2940, 1597, 1488, 1460, 1267, 1240, 1132, 1090, 1022, 1004, 752, 661 |
| 74 | 2-OCH₃-phenyl | $(CH_3)_3C-$ | $CH_3-CO-$ | " | resin | 2965, 1736, 1604, 1496, 1467, 1374, 1248, 1140, 1025, 759, 685, 667 |
| 75 | 2-OCH₃-phenyl | $(CH_3)_3-$ | $Cl-CH_2-CO-$ | " | resin | 2955, 1750, 1491, 1286, 1248, 1165, 980, 754 |
| 76 | 3-CH₃-4-OCH₃-phenyl | $(CH_3)_3C-$ | $CH_3-CO-$ | " | 103–105 | |
| 77 | 1-naphthyl | $CH_3-$ | $CH_3$ | " | resin | 2960, 1496, 1440, 1270, 1201, 1134, 1055, 742, 696, 678 |
| 78 | 1-naphthyl | $CH_3-$ | $n-C_4H_9$ | " | resin | 2945, 2915, 2855, 1595, 1267, 1132, 1089, 773, 676 |
| 79 | 1-naphthyl | $CH_3-$ | $C_6H_5-CH_2-$ | " | resin | 2965, 2925, 1495, 1452, 1272, 1135, 1060, 777, 736, 699 |
| 80 | 1-naphthyl | $(CH_3)_3C-$ | allyl | " | resin | 2950, 2865, 1498, 1363, 1272, 1135, 1082, 1050, 1005, 993, 977, 679 |

TABLE-continued $$R^1-CH-CH_2-CH-R^2$$
$$\phantom{R^1-CH}|\phantom{-CH_2-}|$$
$$\phantom{R^1-C}Az\phantom{-CH_2-C}O-R^3$$

| Ex. no. | R¹ | R² | R³ | Az | m.p./°C. | IR (film) [cm⁻¹] |
|---|---|---|---|---|---|---|
| 81 | (CH₃)₃C— |  | CH₃— | " | 124–125 | |
| 82 | (CH₃)₃C— |  |  | " | resin | 3050, 2955, 2860, 1590, 1498, 1365, 1270, 1135, 1080, 800, 775, 680 |
| 83 | (CH₃)₃C— |  | CH₃— | " | 53–55 | |
| 84 | (CH₃)₃C— |  | CH₃ | " | resin | 3090, 2950, 2810, 1493, 1362, 1266, 1132, 1080, 1003, 700, 675, 660 |
| 85 | (CH₃)₃C— |  |  | " | resin | 3100, 2960, 2865, 1498, 1366, 1270, 1136, 1075, 925, 700, 680, 665 |
| 86 | (CH₃)₃C— | 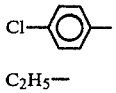 | 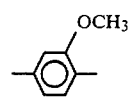 | " | resin | 3100, 2960, 2870, 1595, 1500, 1490, 1366, 1270, 1136, 1080, 1012, 700 |
| 87 | 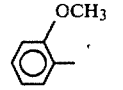 | CH₃— | C₂H₅— | " | resin | 2965, 1491, 1460, 1245, 1150, 1090, 1025, 752 |
| 88 |  | CH₃— | 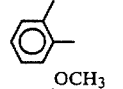 | " | resin | 2952, 1596, 1488, 1458, 1267, 1241, 1135, 1022, 752 |
| 89 | 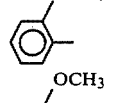 | CH₃— | n-C₄H₉ | " | resin | 2952, 2925, 1492, 1461, 1270, 1244, 1187, 1088, 1025, 751 |
| 90 | 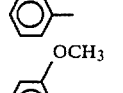 | CH₃— | n-C₆H₁₃ | " | resin | 2920, 1490, 1460, 1269, 1243, 1134, 1088, 1023, 751, 676, 659 |
| 91 | 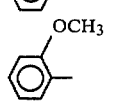 | CH₃— | n-C₈H₁₇ | " | resin | 2918, 1490, 1460, 1269, 1242, 1134, 1090, 1025, 751 |
| 92 | 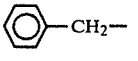 | CH₃ | 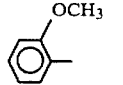 | " | resin | 2910, 1486, 1457, 1370, 1239, 1131, 1021, 746, 691 |
| 93 | 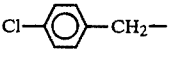 | CH₃— | 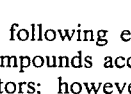 | " | resin | 2952, 2920, 2850, 1596, 1488, 1404, 1240, 1181, 1011, 804, 751 |
| 94 | OCH₃ | CH₃— | (CH₃)₃C—CO— | " | resin | 2960, 1721, 1490, 1460, 1278, 1243, 1160, 1135, 1024, 752 |

The following examples demonstrate the action of the compounds according to the invention as growth regulators; however, further applications as growth regulators are not excluded.

Plastic pots 12.5 cm in diameter were filled with a peat substrate provided with sufficient nutrients, and test plants grown therein under greenhouse conditions. In the preemergence treatment, the substances to be tested were sprayed, as aqueous formulations at various concentrations, onto the surface of the soil on the day the seeds were sown. In the leaf treatment, the plants were sprayed as aqueous formulations at various concentrations when the plants were at a height of approx. 10 cm. The growth-regulating action observed was confirmed at the end of the experiment by height measurements. The values obtained were compared with those for untreated plants. The comparative agents employed were the prior art compounds CCC and A.

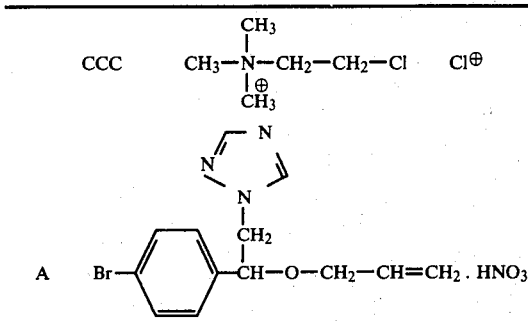

1. Influence on the height of monocotyledonous plants
1.1 Spring wheat, "Kolibri" variety; preemergence treatment
Duration of expt.: 14 days

| Compound no. | Concentration in mg of active ingredient per vessel | Growth height cm | % |
|---|---|---|---|
| Untreated (control) | — | 28.8 | 100 |
| CCC | 3 | 20.5 | 71.2 |
|  | 12 | 16.0 | 55.6 |
| 17 | 3 | 16.5 | 57.3 |
|  | 12 | 7.0 | 24.3 |
| 18 | 3 | 20.5 | 71.2 |
|  | 12 | 14.0 | 48.6 |

1.2 Spring wheat, "Kolibri" variety; preemergence treatment
Duration of expt.: 14 days

| Compound no. | Concentration in mg of active ingredient per vessel | Growth height cm | % |
|---|---|---|---|
| Untreated (control) | — | 30.4 | 100 |
| CCC | 3 | 20.0 | 65.8 |
|  | 12 | 19.0 | 62.5 |
| 3 | 3 | 20.0 | 65.8 |
|  | 12 | 17.0 | 55.9 |
| 59 | 3 | 17.5 | 57.6 |
|  | 12 | 15.0 | 49.3 |

1.3 Spring wheat, "Kolibri" variety; preemergence treatment
Duration of expt.: 15 days

| Compound no. | Concentration in mg of active ingredient per vessel | Growth height cm | % |
|---|---|---|---|
| Untreated (control) | — | 31.3 | 100 |
| CCC | 3 | 22.0 | 70.3 |
|  | 12 | 20.5 | 65.5 |
| 34 | 3 | 18.0 | 57.5 |
|  | 12 | 6.0 | 19.2 |

1.4 Spring wheat, "Kolibri" variety; preemergence treatment
Duration of expt.: 12 days

| Compound no. | Concentration in mg of active ingredient per vessel | Growth height cm | % |
|---|---|---|---|
| Untreated (control) | — | 27.8 | 100 |
| CCC | 3 | 22.5 | 80.9 |
|  | 12 | 19.0 | 68.4 |
| A | 3 | 26.0 | 93.5 |
|  | 12 | 19.0 | 68.4 |
| 57 | 3 | 21.5 | 77.3 |
|  | 12 | 15.0 | 54.0 |

1.5 Spring wheat, "Kolibri" variety; preemergence treatment
Duration of expt.: 14 days

| Compound no. | Concentration in mg of active ingredient per vessel | Growth height cm | % |
|---|---|---|---|
| Untreated (control) | — | 30.4 | 100 |
| CCC | 3 | 20.0 | 65.8 |
|  | 12 | 19.0 | 62.5 |
| 58 | 3 | 20.0 | 65.8 |
|  | 12 | 16.0 | 52.6 |

1.6 Spring barley, "Union" variety; preemergence treatment
Duration of expt.: 14 days

| Compound no. | Concentration in mg of active ingredient per vessel | Growth height cm | % |
|---|---|---|---|
| Untreated (control) | — | 28.3 | 100 |
| CCC | 3 | 24.0 | 84.8 |
|  | 12 | 22.0 | 77.7 |
| 17 | 3 | 13.0 | 45.9 |
|  | 12 | 5.0 | 17.7 |
| 18 | 3 | 25.0 | 88.3 |
|  | 12 | 14.0 | 49.5 |

1.7 Spring barley, "Union" variety; preemergence treatment
Duration of expt.: 14 days

| Compound no. | Concentration in mg of active ingredient per vessel | Growth height cm | % |
|---|---|---|---|
| Untreated (control) | — | 25.7 | 100 |
| CCC | 3 | 21.0 | 81.7 |
|  | 12 | 20.0 | 77.8 |
| 25 | 3 | 22.0 | 85.3 |
|  | 12 | 17.0 | 65.9 |

1.8 Oats, "Flamingskrone" variety; preemergence treatment
Duration of expt.: 16 days

| Compound no. | Concentration in mg of active ingredient per vessel | Growth height cm | % |
|---|---|---|---|
| Untreated (control) | — | 25.8 | 100 |
| CCC | 3 | 24.0 | 93.0 |
|  | 12 | 22.5 | 87.2 |
| 25 | 3 | 22.0 | 85.3 |
|  | 12 | 17.0 | 65.9 |
| 40 | 3 | 21.0 | 81.4 |
|  | 12 | 19.0 | 73.6 |

2. Influence on the height of dicotyledons
2.1 Spring rape, "Petronova" variety; preemergence treatment
Duration of expt.: 16 days

| Compound no. | Concentration in mg of active ingredient per vessel | Growth height cm | % |
|---|---|---|---|
| Untreated (control) | — | 20.0 | 100 |
| CCC | 3 | 18.0 | 90.0 |
|  | 12 | 17.5 | 87.5 |
| 3 | 3 | 15.5 | 77.5 |
|  | 12 | 14.0 | 70.0 |
| 59 | 3 | 17.5 | 87.5 |
|  | 12 | 15.0 | 75.0 |

2.2 Spring rape, "Cosa" variety; preemergence treatment
Duration of expt.: 16 days

| Compound no. | Concentration in mg of active ingredient per vessel | Growth height cm | % |
|---|---|---|---|
| Untreated (control) | — | 17.3 | 100 |
| CCC | 3 | 16.5 | 95.4 |
|  | 12 | 16.5 | 95.4 |
| 30 | 3 | 15.5 | 89.6 |
|  | 12 | 14.5 | 83.8 |
| 31 | 3 | 15.5 | 89.6 |
|  | 12 | 13.0 | 75.1 |
| 32 | 3 | 15.5 | 89.6 |
|  | 12 | 13.5 | 78.0 |

2.3 Spring rape, "Cosa" variety; preemergence treatment
Duration of expt.: 19 days

| Compound no. | Concentration in mg of active ingredient per vessel | Growth height cm | % |
|---|---|---|---|
| Untreated (control) | — | 18.0 | 100 |
| CCC | 3 | 16.5 | 91.7 |
|  | 12 | 16.5 | 91.7 |
| 34 | 3 | 16.5 | 91.7 |
|  | 12 | 15.3 | 85.0 |

2.4 Spring rape, "Petronova" variety; preemergence treatment
Duration of expt.: 16 days

| Compound no. | Concentration in mg of active ingredient per vessel | Growth height cm | % |
|---|---|---|---|
| Untreated (control) | — | 14.8 | 100 |
| CCC | 3 | 14.0 | 94.6 |
|  | 12 | 13.0 | 87.8 |
| 57 | 3 | 13.5 | 91.2 |
|  | 12 | 10.5 | 71.0 |

2.5 Spring rape, "Petronova" variety; preemergence treatment
Duration of expt.: 16 days

| Compound no. | Concentration in mg of active ingredient per vessel | Growth height cm | % |
|---|---|---|---|
| Untreated (control) | — | 20.0 | 100 |
| CCC | 3 | 18.0 | 90.0 |
|  | 12 | 17.5 | 87.5 |
| 58 | 3 | 16.5 | 82.5 |
|  | 12 | 14.0 | 70.0 |

2.6 Spring rape, "Cosa" variety; leaf treatment
Duration of expt.: 19 days

| Compound no. | Concentration in mg of active ingredient per vessel | Growth height cm | % |
|---|---|---|---|
| Untreated (control) | — | 19.4 | 100 |
| CCC | 1.5 | 17.0 | 87.6 |
|  | 6 | 16.0 | 82.5 |
| 36 | 1.5 | 16.5 | 85.1 |
|  | 6 | 14.0 | 72.2 |
| 37 | 1.5 | 16.5 | 85.1 |
|  | 6 | 15.5 | 79.9 |

2.7 Spring rape, "Petronova" variety; leaf treatment
Duration of expt.: 19 days

| Compound no. | Concentration in mg of active ingredient per vessel | Growth height cm | % |
|---|---|---|---|
| Untreated (control) | — | 17.1 | 100 |
| CCC | 1.5 | 16.0 | 93.6 |
|  | 6 | 15.5 | 90.6 |
| A | 1.5 | 17.0 | 99.4 |
|  | 6 | 15.5 | 90.6 |
| 70 | 1.5 | 13.8 | 80.7 |
|  | 6 | 12.3 | 71.9 |

EXAMPLE 95

90 parts by weight of compound 1 is mixed with 10 parts by weight of N-methyl-α-pyrrolidone. A mixture is obtained which is suitable for application in the form of very fine drops.

EXAMPLE 96

20 parts by weight of compound 2 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

EXAMPLE 97

20 parts by weight of compound 3 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

EXAMPLE 98

20 parts by weight of compound 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

EXAMPLE 99

20 parts by weight of compound 2 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

EXAMPLE 100

3 parts by weight of compound 3 is intimately mixed with 97 parts by weight of particulate kaolin. A dust is obtained containing 3% by weight of the active ingredient.

EXAMPLE 101

30 parts by weight of compound 4 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 102

40 parts by weight of compound 1 is intimately mixed with 10 parts of the sodium salt of a phenolsulfonic acid-urea-formaldehyde condensate, 2 parts of silica gel and 48 parts of water to give a stable aqueous dispersion. Dilution in 100,000 parts by weight of water gives an aqueous dispersion containing 0.04 wt% of active ingredient.

EXAMPLE 103

20 parts of compound 2 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

We claim:

1. A γ-azolyl compound of the formula

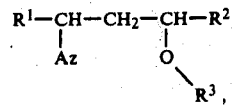

wherein $R^1$ is unsubstituted phenyl or phenyl substituted by fluoro, chloro, bromo, nitro, trifluoromethyl, alkyl of 1 to 4 carbon atoms, alkoxy of 1 to 4 carbon atoms, or by alkenyl of 1 to 4 carbon atoms; $R^2$ is alkyl of 1 to 8 carbon atoms; $R^3$ is alkyl of 1 to 8 carbon atoms, unsubstituted or chloro-substituted alkenyl of 2 to 5 carbon atoms, alkynyl of 3 to 4 carbon atoms, benzyl which is unsubstituted or substituted by fluoro, chloro, bromo, nitro, trifluoromethyl, or by alkyl or alkoxy of 1 to 4 carbon atoms and Az denotes 1,2,4-triazolyl or 1,2,3-triazolyl.

2. A γ-azolyl compound as claimed in claim 1, selected from the group consisting of 1-(2-chlorophenyl)-1-(1,2,4-triazolyl-(1))-3-allyloxybutane, 1-(2-chlorophenyl)-1-(1,2,4-triazolyl-(1))-3-(1-propoxy)-butane, 1-(2-chlorophenyl)-1-(1,2,4-triazolyl-(1))-3-(1-butoxy)-butane, 1-(4-chlorophenyl)-1-(1,2,4-triazolyl-(1))-3-ethoxybutane, 1-(4-chlorophenyl)-1-(1,2,4-triazolyl-(1))-3-(1-pentyloxy)-butane, and 1-(2,4-dichlorophenyl)-1-(1,2,4-triazolyl-(1))-3-allyloxy-4,4-dimethyl-pentane.

* * * * *

UNITED STATES PATENT AND TRADEMARK OFFICE
CERTIFICATE OF CORRECTION

PATENT NO. : 4,278,800
DATED : July 14, 1981
INVENTOR(S) : Costin Rentzea, Hubert Sauter, Eberhard Ammermann, Gerd Heilen, and Johann Jung It is certified that error appears in the above—identified patent and that said Letters Patent is hereby corrected as shown below:

On the cover page, under U.S. Patent Documents, the last reference cited should be U.S. Patent --3,647,814-- and not "8,647,814".

Signed and Sealed this

Ninth Day of March 1982

[SEAL]

*Attest:*

*Attesting Officer*

GERALD J. MOSSINGHOFF

*Commissioner of Patents and Trademarks*